US010835284B2

(12) United States Patent
Geisz et al.

(10) Patent No.: US 10,835,284 B2
(45) Date of Patent: Nov. 17, 2020

(54) METHOD AND SYSTEM FOR CONTROLLING PRESSURIZATION OF A PATIENT CAVITY USING CAVITY DISTENSION MEASURED BY A PRESSURE SENSOR OF A TROCAR (71) Applicant: Lexion Medical, LLC, St. Paul, MN (US)

(72) Inventors: Carl M. Geisz, Edina, MN (US); Douglas E. Ott, Macon, GA (US)

(73) Assignee: Lexion Medical, LLC, St. Paul, MN (US)

( * ) Notice: Subject to any disclaimer, the term of this patent is extended or adjusted under 35 U.S.C. 154(b) by 573 days.

(21) Appl. No.: 15/293,013

(22) Filed: Oct. 13, 2016

(65) Prior Publication Data

US 2018/0103977 A1   Apr. 19, 2018

(51) Int. Cl.
    A61B 17/34      (2006.01)
    A61B 17/00      (2006.01)
    (Continued)

(52) U.S. Cl.
    CPC ........ A61B 17/34 (2013.01); A61B 17/00234 (2013.01); A61B 17/3423 (2013.01);
    (Continued)

(58) Field of Classification Search
    CPC ............... A61B 17/34; A61B 17/3474; A61B 17/00234; A61B 17/3476; A61B 17/3445;
    (Continued)

(56) References Cited

U.S. PATENT DOCUMENTS 5,147,316 A * 9/1992 Castillenti ............. A61B 17/34
                                                      604/164.04
5,209,721 A    5/1993 Wilk
                (Continued)

FOREIGN PATENT DOCUMENTS

EP        1 109 486       5/2000
EP        2 825 840       9/2013
WO    WO2013011398        1/2013

OTHER PUBLICATIONS

PCT International Search Report; appl. No. PCT/US17/56322; 2 pages, dated Dec. 11, 2017.
(Continued)

Primary Examiner — Kevin C Sirmons
Assistant Examiner — Alexandra Lalonde
(74) Attorney, Agent, or Firm — Baker Botts L.L.P.

(57) ABSTRACT

According to one embodiment, a method includes positioning a trocar having a pressure sensor in or on the trocar into a patient cavity such that distension of the patient cavity causes an altitude of the pressure sensor to increase. The method also includes distending the patient cavity by supplying an insufflation gas to the patient cavity, thereby increasing an altitude of the pressure sensor from a first altitude to a second altitude. The method also includes determining a change in pressure at the pressure sensor resulting from increasing the altitude of the pressure sensor from the first altitude to the second altitude and controlling the supply of insufflation gas to the patient cavity in response to the determined change in pressure resulting from increasing the altitude of the pressure sensor from the first altitude to the second altitude.

16 Claims, 5 Drawing Sheets (51) Int. Cl.
*A61M 13/00* (2006.01)
*A61B 90/00* (2016.01)

(52) U.S. Cl.
CPC ....... *A61B 17/3474* (2013.01); *A61M 13/003* (2013.01); *A61B 2017/00022* (2013.01); *A61B 2090/032* (2016.02); *A61B 2560/0242* (2013.01); *A61B 2562/0247* (2013.01); *A61M 2205/3344* (2013.01)

(58) Field of Classification Search
CPC ............ A61B 17/3423; A61B 17/3494; A61B 17/003; A61B 2090/064; A61B 2090/08021; A61B 2017/00022; A61B 2017/3449; A61B 2017/348; A61B 2017/3492; A61B 2562/0247; A61B 2034/2055; A61B 2034/2065; A61B 5/103; A61B 5/11; A61M 13/003; A61M 13/006; A61M 2202/0225; A61M 2205/3344; A61M 2205/0233; A61M 2205/3341; A61M 2205/3327; A61M 2205/33; A61M 2205/3303; A61M 2205/3331; A61M 25/04; A61M 2025/0002; A61M 2025/0003; A61M 31/00; A61M 2210/1021; A61M 2230/00; A61M 2230/005
See application file for complete search history.

(56) References Cited

U.S. PATENT DOCUMENTS

| | | | |
|---|---|---|---|
| 5,389,077 A | 2/1995 | Melinyshyn | |
| 5,423,741 A * | 6/1995 | Frank | A61M 13/003 604/23 |
| 5,427,114 A | 6/1995 | Colliver | |
| 5,676,155 A * | 10/1997 | Novak | A61M 13/003 600/560 |
| 6,295,877 B1 | 10/2001 | Aboul-Hosn | |
| 6,299,592 B1 | 10/2001 | Zander | |
| 6,905,489 B2 | 6/2005 | Mantell | |
| 7,285,112 B2 | 10/2007 | Stubbs | |
| 7,722,558 B2 | 5/2010 | Ott | |
| 8,216,189 B2 | 7/2012 | Stubbs | |
| 8,235,940 B2 | 8/2012 | Davis | |
| 8,715,219 B2 | 5/2014 | Stearns | |
| 9,138,549 B2 | 9/2015 | Pagel et al. | |
| 2004/0102733 A1 | 5/2004 | Naimark | |
| 2005/0115043 A1 | 6/2005 | Maeshima | |
| 2010/0152664 A1* | 6/2010 | Davis | A61B 17/3494 604/164.03 |
| 2011/0218484 A1* | 9/2011 | Zemlok | A61M 13/00 604/26 |
| 2012/0184897 A1 | 7/2012 | Poll | |
| 2012/0245511 A1 | 9/2012 | Stearns et al. | |
| 2015/0005698 A1* | 1/2015 | Yokoyama | A61B 17/00491 604/24 |
| 2015/0290387 A1 | 10/2015 | Mollstam | |

OTHER PUBLICATIONS

Dr. Asif Iqbal, et al.; *Effects of Co2 Pneumoperitoneum in Patients Undergoing Short Laparoscopic Gynaecology Procedures: IOSR Journal of Dental and Medical Sciences*; 2279-0861, vol. 15; Issue 6 Ver. VIII; pp. 11-15; www.iosrjournals.org, Jun. 2016.
PCT Written Opinion of the International Searching Authority; appl. No. PCT/US17/56322; 7 pages, dated Dec. 11, 2017.
Rawandale, Pav; *Rawandale's Laparoscopic Port Placement Barometer*; IN-MUM-2014-00059A; abstract; statement of invention; 7 pages, Jan. 31, 2014.
Sanaz Hariri Tabrizi, et al.; *A Preliminary Study on the Use of an Automatic Trocar for LAparoscopic Surgery* (ATLAS System); vol. 2, Issue 4; 6 pages, Dec. 2015.

* cited by examiner

METHOD AND SYSTEM FOR CONTROLLING PRESSURIZATION OF A PATIENT CAVITY USING CAVITY DISTENSION MEASURED BY A PRESSURE SENSOR OF A TROCAR

TECHNICAL FIELD OF THE INVENTION

The present invention disclosure relates generally to medical procedures and more particularly to a method for controlling pressurization of a patient cavity using cavity distension measured by a pressure sensor of a trocar.

BACKGROUND OF THE INVENTION

Laparoscopic surgery is a standard procedure in hospitals. Abdominal and chest cavity operations are being performed with instruments inserted through small incisions into interior portions of the body. Such laparoscopic procedures are now considered the treatment of choice for operations such as the removal of the gall bladder, spleen, adrenal glands, uterus, and ovaries. These laparoscopic procedures are accomplished via access through a device typically known as a trocar. A trocar facilitates the introduction of laparoscopic instruments into the abdomen or chest of the body. These instruments are typically introduced into regions under fluid pressure. This fluid may be a gas, referred to herein as an insufflation gas.

Providing an insufflation gas into a body cavity is referred to as insufflation. Currently, insufflation is performed by providing a regulated pressurized insufflation gas to the peritoneal cavity via a cannula of the trocar. This insufflation gas, typically carbon dioxide, is supplied to a connection on the trocar tube by a flexible hose attached thereto. The medical instrument going through the innermost tube of the trocar should be sealed relative to the trocar so the insufflation gas will not escape from the patient.

A physician can use a trocar device to introduce different types of instruments into a patient. In order to reduce incisions into the body, typically the insufflation gas is delivered into a body cavity during specific medical procedures or treatment is done via a trocar that also allows insertion of an instrument via the innermost tube of the trocar. The purpose of using such a device is to inflate or distend the body cavity to (1) allow the surgeon to explore the area in which the surgery will be performed and (2) provide a view of the site to be treated or observed.

Insufflation is used in many common procedures including endoscopic surgical procedures, laparoscopic procedures performed on the abdominal cavity and orthoscopic procedures performed on the chest cavity. Additional trocars can be used during the same surgical procedure to remove surgical smoke from the patient cavity or to continuously measure pressure within the body cavity. These trocars typically also allow for the insertion of an instrument via the innermost tube of the trocar.

SUMMARY OF THE INVENTION

According to one embodiment, a method includes positioning a trocar having a pressure sensor in or on the trocar into a patient cavity such that distension of the patient cavity causes an altitude of the pressure sensor to increase. The method also includes distending the patient cavity by supplying an insufflation gas to the patient cavity, thereby increasing an altitude of the pressure sensor from a first altitude to a second altitude. The method also includes determining a change in pressure at the pressure sensor resulting from increasing the altitude of the pressure sensor from the first altitude to the second altitude and controlling the supply of insufflation gas to the patient cavity in response to the determined change in pressure resulting from increasing the altitude of the pressure sensor from the first altitude to the second altitude.

The teachings of the disclosure provide one or more technical advantages. Embodiments of the disclosure may have none, some, or all of these advantages. For example, in some embodiments, a method allows more accurate determination of the optimized gas pressure to achieve required cavity distention. This can avoid over-pressurization of the patient, which could cause a variety of issues including increased CO2 adsorption and reduced blood flow to the peritoneal wall.

Other advantages will be apparent to those of skill in the art.

BRIEF DESCRIPTION OF THE DRAWINGS

For a more complete understanding of embodiments of the disclosure and the potential advantages thereof, reference is now made to the following written description taken in conjunction with the accompanying drawings, in which.

DETAILED DESCRIPTION OF THE INVENTION

The present disclosure relates to a method for monitoring the change in height of the trocar using a pressure sensor. Small pressure sensors are available in the marketplace that can measure absolute barometric pressures. The accuracy of these devices can be well less than 1 Pascal pressure. These pressure sensors have the ability to measure the relative changes in altitude of close to one inch.

By placing a pressure sensor in the gas delivery trocar, which in some cases measures absolute pressure, the relative height of the trocar can be measured during insufflation of the cavity. As pressure builds in the cavity, the abdominal wall begins to lift. The lifting of the abdominal wall slowly creates a pocket or cavity of CO2 gas. Once the cavity has risen to the desired height, the surgeon now has the required visibility to gain access to a target surgical site in the cavity.

Often the surgeon has a difficult time determining the optimized gas pressure to achieve the required cavity distention. The difficulty is due to a number of factors including the patient's cavity size, weight, location of target site, etc. Due to this difficulty, the surgeon will often over-pressurize the patient. This over-pressurization can cause a variety of issues including increased CO2 adsorption and reduced blood flow to the peritoneal wall.

Example embodiments are best understood by referring to FIGS. 1 through 4B of the drawings and the description below, like numerals being used for like and corresponding parts of the various drawings.

Figure 1:
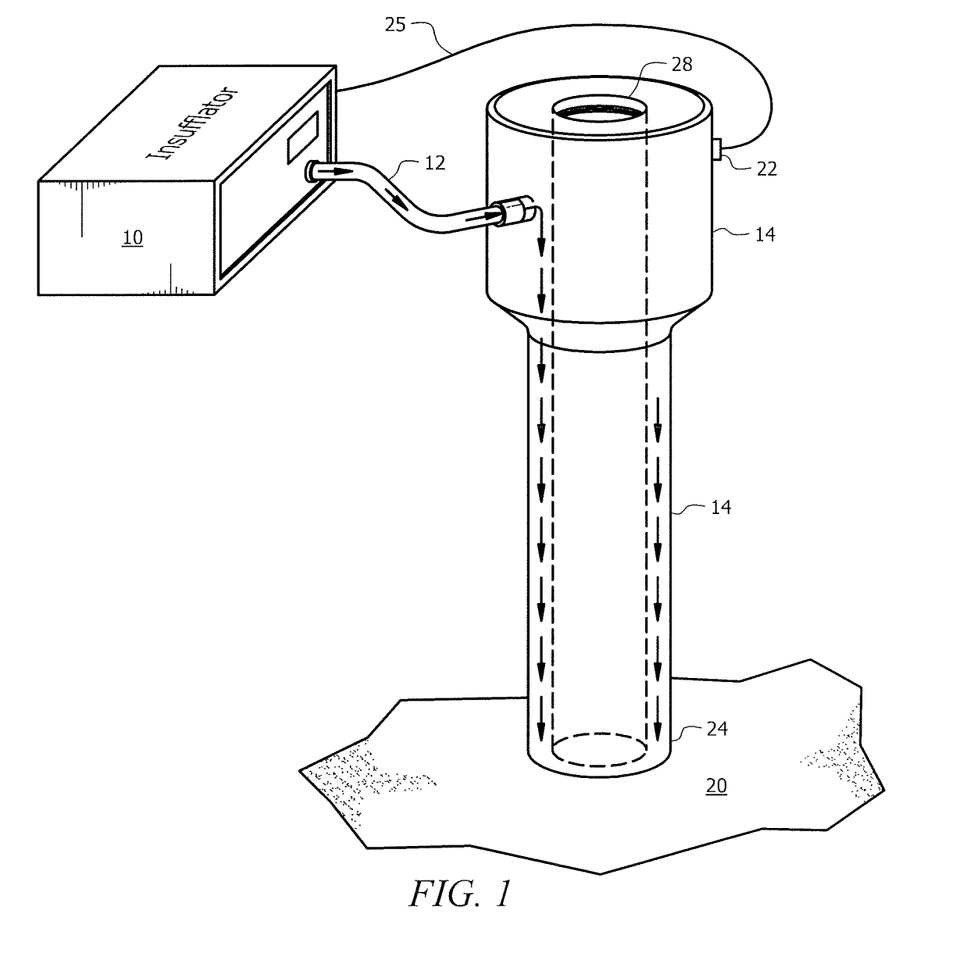
FIG. 1 is a schematic diagram showing the distal end of a trocar having an associated pressure sensor, the distal end placed in the abdominal cavity of a patient.

FIG. 1 is a schematic diagram showing the distal end 24 of a trocar 14 placed in the abdominal cavity 20 of a patient. In general, an insufflator 10 supplies insufflation gas through conduit 12 and trocar 14 to patient cavity 20. Trocar 14 allows insertion of a surgical instrument 28 into patient cavity 20.

Trocar 14 has a pressure sensor 22 on or associated with the trocar 14. The location can be anywhere in or on trocar 14 or associated with trocar 14 such that vertical movement of trocar 14 results in vertical movement of pressure sensor 22; however, as described in greater detail below, in one embodiment pressure sensor is located on the exterior of trocar 14 such that changes of pressure within trocar 14 due to supply of insufflation fluid to patient cavity 20 do not affect the pressure measured by pressure sensor 22. In some embodiments, pressure sensor 22 is an absolute pressure sensor that can measure pressure in patient cavity 20 (if disposed within patient cavity 20) or in the room in which the associated operation is taking place.

Pressure sensor 22 is coupled to insufflator 10 through any suitable technique, including a wired connection 25 or a wireless connection. Pressure sensor supplies pressure data to insufflator 10. Insufflator 10 uses this pressure data to determine the change in height of trocar 14 relative to changes in cavity pressure and thus the resulting change in height of patient cavity 20, as described in greater detail below in conjunction with FIGS. 2A through 4. Based upon this information, insufflator 10 (or other associated device) can determine the optimum, or a close approximation thereof, of the best pressure for the laparoscopic surgery and as a result control the pressure within patient cavity by controlling the pressure of the insufflation gas supplied by insufflator through tube 12. Additional details of certain portions of FIG. 1 are described below.

Insufflator 10 may be any suitable source of insufflation gas at any suitable pressure. Insufflator may adjust the supply of insufflation gas to patient cavity 20 by adjusting the pressure and/or the volume of insufflation gas supplied to patient cavity 20. Insufflator may include appropriate hardware and/or software for processing signals indicative of pressures measured by pressure sensor 22 and processing such signals to convert them into useful information, such as converting them into pressures, heights, and/or other data that can be used control the flow of insufflation gas to patient cavity 20, and further for processing such data to determine a desired pressure and/or volume of insufflation fluid supplied to patient cavity 20 and for effecting such delivery.

Conduit 12 may be any suitable conduit for providing an insufflation gas to a portion of a trocar. An example of conduit 12 includes flexible PVC tubing. The insufflation gas may be any suitable gas used for insufflation purposes. In one example, insufflation case is carbon dioxide.

Trocar 14 may be any suitable trocar through which insufflation fluid may be supplied to a patient cavity. Examples of one or more trocars are provided in U.S. Pat. No. 8,715,219 (the '219 Patent), U.S. Pat. No. 7,285,112 (the '112 Patent), and U.S. Pat. No. 8,216,189 (the '189 Patent), which are hereby incorporated by reference as if fully set forth herein. Trocar 14 may be have a single lumen or may be formed with an inner tubular lumen and an outer tubular lumen such that insufflation fluid may be supplied through one of the lumens but not the other. Further, any of the lumens may be divided into multiple, separate chambers, such that fluid in one chamber does not enter the other chamber. Examples of the above multiple lumens and multiple chambered trocars are described in U.S. application Ser. No. 14/792,873, entitled "Method and System for Gas Maintenance to a Body Cavity Using a Trocar," which is hereby incorporated by reference. Trocar 14 may be open or closed at the distal end 24, as the application of the trocar would allow.

Pressure sensor 22 may be any sensor capable of sensing pressure or a change in pressure. Pressure sensor 22 may measure absolute pressure or a pressure relative to some other pressure. In some embodiments, pressure sensor 22 is an absolute sensor that can measure pressure in patient cavity 20 (if disposed within patient cavity 20) or in the room in which the associated operation is taking place. In particular embodiments, pressure sensor 22 can measure absolute barometric pressures with an accuracy of less than 1 Pascal pressure and therefore have the ability to measure the relative changes in altitude of close to one inch. Such pressure sensors are readily available in the marketplace.

Figure 2A:
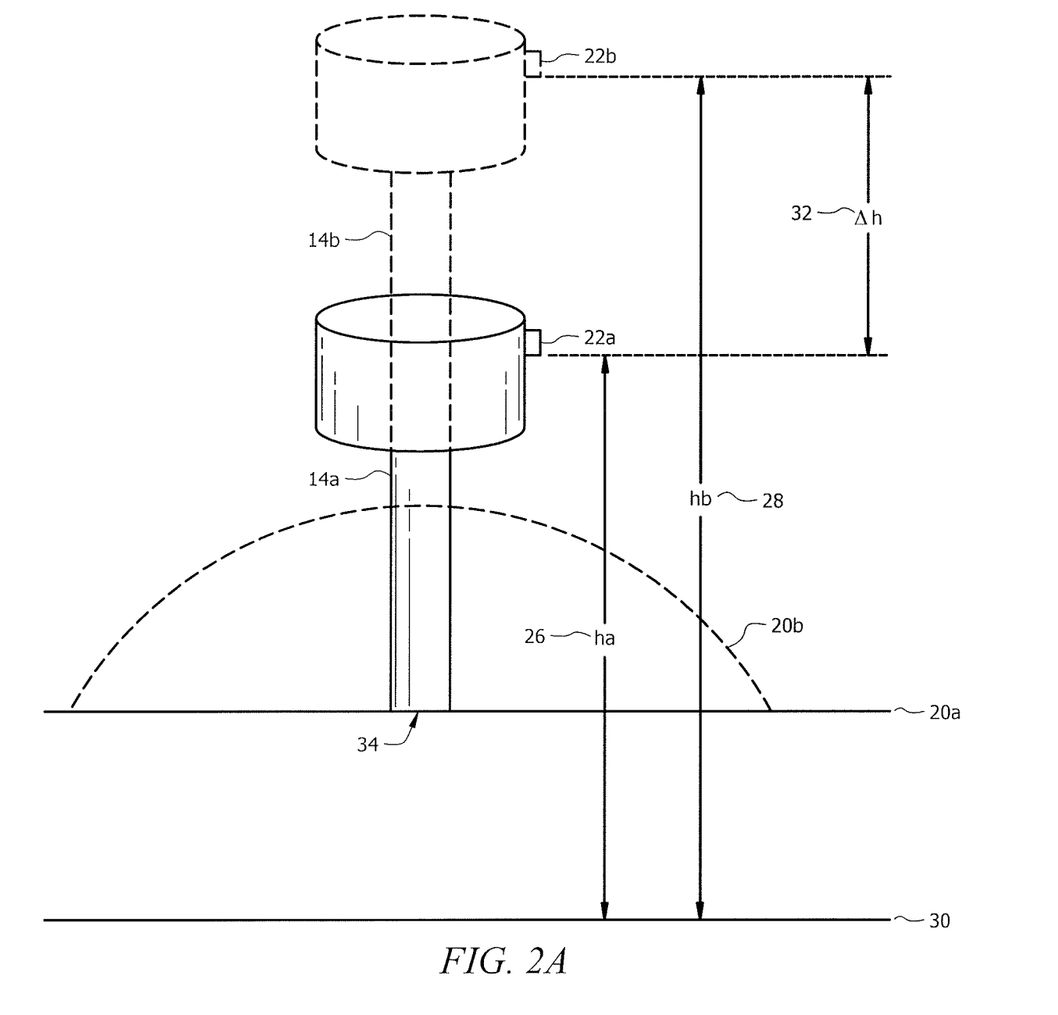
FIGS. 2A and 2B are schematic diagrams of the trocar of FIG. 1 at a first location corresponding to a position in which the trocar is at a low insufflator pressure and at a second location resulting from increased pressure supplied to the patient cavity.
Figure 2B:
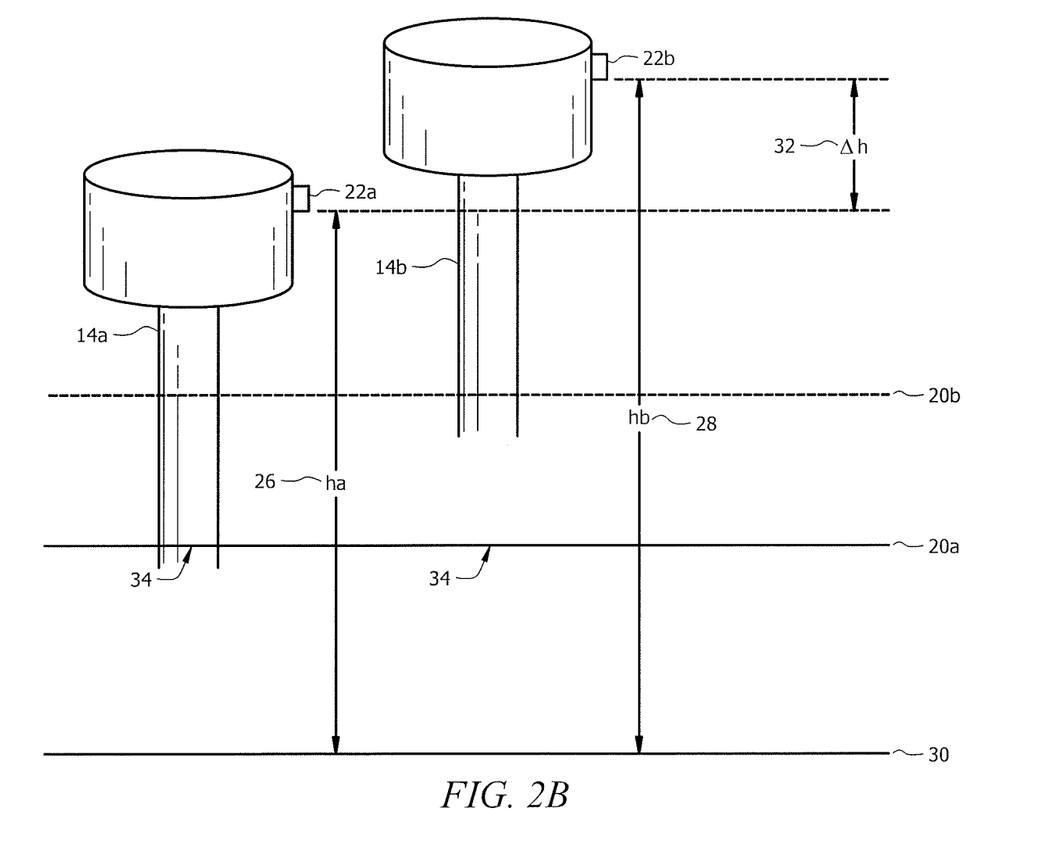

Additional details of the use of trocar 14 and pressure sensor 22 to determine a change in altitude of pressure sensor 22 are described below in conjunction with FIGS. 2A and 2B. FIG. 2A is a schematic diagram of trocar 14 at a first location (denoted by 14a and in solid lines) corresponding to a position in which the trocar 14 is at a low insufflator pressure and at a second location (denoted by 14b and in dotted lines) resulting from increased pressure supplied to the patient cavity. FIG. 2B is analogous to FIG. 2A, but illustrates both trocars 14a and 14b separated horizontally in space in the drawing for clarity of illustration, but additionally corresponding to the same horizontal position, identified by reference numeral 34 in FIG. 2A. It should be appreciated, however, that trocar 14 may move both vertically and horizontally due to distention of the patient cavity.

With reference to FIG. 2A and FIG. 2B, trocar 14a in solid lines corresponds to trocar 14 at a first vertical location. This first location may correspond to a position in which patient cavity 20a is not distended at all or may correspond to a location in which patient cavity 20a is partially distended. Trocar 14b in dotted lines corresponds to trocar 14 at a second vertical location after some distention of patient cavity, shown by dotted line 20b. The altitude "Ha" of pressure sensor 22a on trocar 14a relative to an arbitrary reference point 30, is indicated by reference numeral 26. A corresponding altitude "Hb" of pressure sensor 22b of trocar 14b relative to reference point 30 is indicated by reference numeral 28. The difference between these two altitudes "delta H" is indicated by reference numeral 32.

As can be seen, as patient cavity 20 distends from 20a to 20b due to the supply of insufflation gas to patient cavity 20, trocar 14 and thus pressure sensor 22 also rises in altitude. As described above, pressure sensor 22 is sensitive to changes in altitude and thus can provide a good indication of the relative change in altitude of pressure sensor 22 from a first altitude to a second altitude, which is indicative of the amount of distension of patient cavity 20 (indicated by dotted line 20b). Due to the elasticity of the patient's cavity 20, higher pressures will start to lift the patient cavity less and less. Based upon the height increase (delta H) versus the cavity pressure a curve can be determined to optimized pressure, in one embodiment. In other embodiments, using this resulting change in pressure or change in altitude may be used in other manners to control insufflation gas supplied to patient cavity or to assist in other decisions, as described in greater detail below.

Figure 3A:
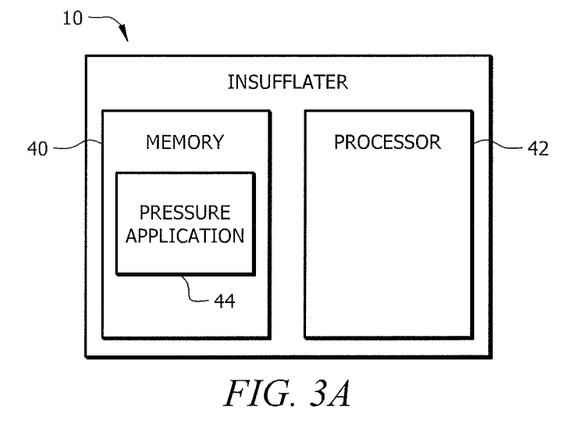
FIGS. 3A and 3B are block diagrams illustrating additional details of components of the system of FIG. 1 that may be used to effect pressure determination and resulting actions.
Figure 3B:
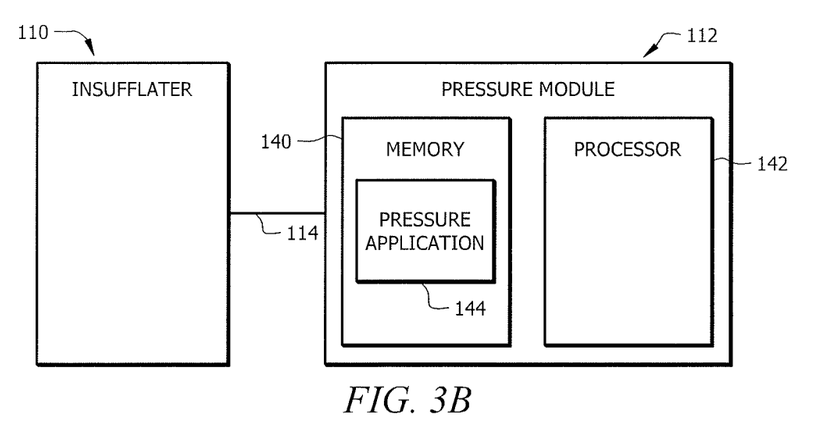

FIGS. 3A and 3B are block diagrams illustrating additional details of components of the system of FIG. 1 that may be used to effect pressure determination and resulting actions. FIG. 3A illustrates additional details of insufflator 10, according to one embodiment. In this embodiment, insufflator 10 includes a memory 40 and a processor 42 communicatively coupled to the memory 40. Memory 40 stores a pressure application 44, which may include logic for effecting pressure and altitude determination as described with respect to the other FIGURES as well as control of the supply of insufflation gas to patient cavity 20. FIG. 3B illustrates an alternative embodiment of the system of FIG. 1 in which an insufflator 110 includes only standard features and is communicatively coupled through a connection 114 to a pressure module 112. Pressure module 112 includes components analogous to those described with respect to FIG. 3A, including a memory 140 and processor 142, but are included in this stand-alone pressure module. Connection 114 between insufflator 110 and pressure module 112 may be wired or wireless. It will be understood that although a software-based system is illustrated in FIGS. 3A and 3B the logic described herein could instead be implemented through hardware circuits or a combination of hardware and software.

Figure 4:
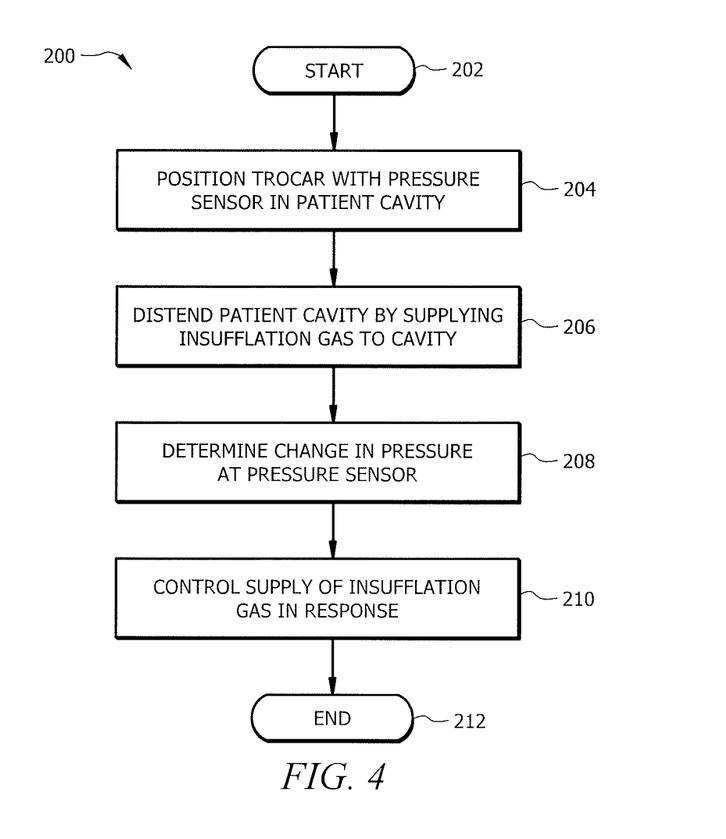
FIG. 4 is a flow chart illustrating a method that includes use of a pressure sensor associated with a trocar.

FIG. 4 is a flow chart illustrating a method 200 that includes use of a pressure sensor associated with a trocar. The method may utilize structural items such as those described in FIGS. 1A through 3B or may use alternative structural items. Computational steps described below may be performed by any suitable computation device, including insufflator 10 and pressure module 112, for example.

The method begins at step 202.

At step 204, a trocar, such as trocar 14, having a pressure sensor, such as pressure sensor 22, in or on the trocar is positioned into a patient cavity, such as patient cavity 20, such that distension of the patient cavity 20 causes an altitude of the pressure sensor to increase. The pressure sensor may be positioned on the exterior or interior of the trocar and may be located within or external to the patient cavity.

At step 206, the method includes distending the patient cavity by supplying an insufflation gas to the patient cavity, thereby increasing an altitude of the pressure sensor from a first altitude to a second altitude. One example of this distension is shown in FIGS. 2A and 2B. In one example, the insufflation gas is supplied by an insufflator, such as insufflator 10, through the associated trocar.

At step 208, the method includes determining a change in pressure at the pressure sensor resulting from increasing the altitude of the pressure sensor from the first altitude to the second altitude. As described above, such actions may be performed by a pressure control application associated with or part of insufflator 10, or by other devices. The determination of the change in pressure may be effected according to a variety of approaches. For example, in one embodiment, the atmospheric pressure at each altitude is measured and a difference is determined. As another example, the pressure difference may be determined by measuring a pressure at the first and second altitudes, which may or may not be a function of atmospheric pressure and may not be the same as atmospheric pressure, and then calculating a difference. In any of the approaches, the first altitude may be an altitude of the pressure sensor after positioning the trocar into the patient cavity and prior to the supplying of insufflation gas to the patient cavity, or alternatively may be the altitude of pressure sensor after positioning the trocar into the patient cavity and after supplying some insufflation gas into the patient cavity.

At step 210, the method includes controlling the supply of insufflation gas to the patient cavity in response to the determined change in pressure resulting from increasing the altitude of the pressure sensor from the first altitude to the second altitude. This may include determining that the pressure or amount of insufflation gas supplied to the patent cavity may be reduced and/or determining that the patient cavity is sufficiently distended such that the pressure or amount of the insufflation gas supplied to the patient cavity may be reduced. Further, the change in altitude of the pressure sensor and/or the patient cavity may be assessed to determine that the patient cavity is sufficiently distended. The control may also include, in some embodiments, comparing the change in the first altitude and the second altitude with a pressure or change in pressure in the patient cavity and/or determining a ratio of the determined change in pressure resulting from increasing the altitude of the pressure sensor from the first altitude to the second altitude to a pressure or change in pressure within the patient cavity and basing a decision on the control of the insufflation gas based on that decision. The control may also include, in some embodiments, determining the change in altitude of the pressure sensor from the first altitude to the second altitude from the determined change in pressure, comparing the determined change in altitude with a pressure or change in pressure in the patient cavity, and controlling the supply of insufflation gas to the patient cavity in response to the comparison.

Step 210 may be omitted entirely, or, alternatively, replaced with merely determining a change in altitude from the first altitude to the second altitude or determining that the patient cavity is sufficiently distended for surgery. Also, step 210 may be replaced with controlling the supply of insufflation gas to the patient cavity based at least in part on the determined amount of distension of the patient cavity. Further, step 210 may be replaced with simply displaying a pressure setting at which a surgeon may set the pressure of the insufflation gas to be supplied to a patient cavity. This display may be on the insufflator or other device.

The method concludes at step 212.

Thus, a method and system have been described that For example, in some embodiments, a method allows more accurate determination of the optimized gas pressure to achieve required cavity distention. This can avoid over-pressurization of the patient, which could cause a variety of issues including increased CO2 adsorption and reduced blood flow to the peritoneal wall.

What is claimed is:

1. A method comprising:
   positioning a trocar having a pressure sensor in or on the trocar into a patient cavity such that distension of the patient cavity causes an altitude of the pressure sensor to increase;
   distending the patient cavity by supplying an insufflation gas to the patient cavity, thereby increasing the altitude of the pressure sensor from a first altitude to a second altitude;
   determining a change in atmospheric pressure at the pressure sensor resulting from increasing the altitude of the pressure sensor from the first altitude to the second altitude by measuring, by the pressure sensor, atmospheric pressure at the first altitude and at the second altitude;

controlling the supply of insufflation gas to the patient cavity in response to the determined change in atmospheric pressure resulting from increasing the altitude of the pressure sensor from the first altitude to the second altitude.

2. The method of claim 1, wherein the first altitude is an altitude of the pressure sensor after positioning the trocar into the patient cavity and prior to the supplying of insufflation gas to the patient cavity.

3. The method of claim 1, wherein the first altitude is an altitude of pressure sensor after positioning the trocar into the patient cavity and after supplying insufflation gas into the patient cavity.

4. The method of claim 1, wherein controlling the supply of insufflation gas to the patient cavity in response to the determined change in atmospheric pressure resulting from increasing the altitude of the pressure sensor from the first altitude to the second altitude comprises determining that a pressure or amount of insufflation gas supplied to the patent cavity may be reduced.

5. The method of claim 1, wherein controlling the supply of insufflation gas to the patient cavity in response to the determined change in atmospheric pressure resulting from increasing the altitude of the pressure sensor from the first altitude to the second altitude comprises determining that the patient cavity is sufficiently distended such that a pressure or amount of the insufflation gas supplied to the patient cavity may be reduced.

6. The method of claim 5, wherein determining that the patient cavity is sufficiently distended such that the pressure or amount of the insufflation gas supplied to the patient cavity may be reduced comprises determining a change in altitude of the pressure sensor from the first altitude to the second altitude.

7. The method of claim 1, wherein the pressure sensor is positioned on the exterior of the trocar.

8. The method of claim 1, wherein the insufflation gas is supplied to the patient cavity through the trocar.

9. The method of claim 1, wherein the pressure sensor located in or on the trocar is further located external to the patient cavity.

10. The method of claim 1, wherein controlling the supply of insufflation gas to the patient cavity in response to the determined change in atmospheric pressure resulting from increasing the altitude of the pressure sensor from the first altitude to the second altitude further comprises comparing a change in the first altitude and the second altitude with at least one of any pressure within the patient cavity and any changes in pressure within the patient cavity.

11. The method of claim 1, wherein controlling the supply of insufflation gas to the patient cavity in response to the determined change in atmospheric pressure resulting from increasing the altitude of the pressure sensor from the first altitude to the second altitude further comprises:

determining a change in altitude of the pressure sensor from the first altitude to the second altitude from the determined change in pressure;

comparing the determined change in altitude with at least one of any pressure within the patient cavity and any change in pressure within the patient cavity; and controlling the supply of insufflation gas to the patient cavity in response to the comparison.

12. A method comprising:

positioning a trocar having a pressure sensor in or on the trocar into a patient cavity such that distension of the patient cavity causes an altitude of the pressure sensor to increase;

distending the patient cavity by supplying an insufflation gas to the patient cavity, thereby increasing the altitude of the pressure sensor from a first altitude to a second altitude;

determining a change in pressure at the pressure sensor resulting from increasing the altitude of the pressure sensor from the first altitude to the second altitude;

controlling the supply of insufflation gas to the patient cavity in response to the determined change in pressure resulting from increasing the altitude of the pressure sensor from the first altitude to the second altitude; and wherein controlling the supply of insufflation gas to the patient cavity in response to the determined change in pressure resulting from increasing the altitude of the pressure sensor from the first altitude to the second altitude further comprises determining a change in altitude of the pressure sensor from the first altitude to the second altitude.

13. A method comprising:

positioning a trocar having a pressure sensor in or on the trocar into a patient cavity such that distension of the patient cavity causes an altitude of the pressure sensor to increase;

distending the patient cavity by supplying an insufflation gas to the patient cavity, thereby increasing the altitude of the pressure sensor from a first altitude to a second altitude; and determining a change in atmospheric pressure at the pressure sensor resulting from increasing the altitude of the pressure sensor from the first altitude to the second altitude by measuring, by the pressure sensor, atmospheric pressure at the first altitude and at the second altitude.

14. The method of claim 13, and further comprising, in response to determining the change in pressure, determining the increase in altitude from the first altitude to the second altitude.

15. The method of claim 13, and further comprising, in response to determining the change in pressure, determining that the patient cavity is sufficiently distended for surgery.

16. The method of claim 13, and further comprising displaying a pressure setting at which the insufflation gas should be supplied to the patient cavity.

* * * * *